(12) United States Patent
Hunter et al.

(10) Patent No.: US 11,969,367 B2
(45) Date of Patent: Apr. 30, 2024

(54) PROSTHETIC SOCKET

(71) Applicant: EPIC INVENTING, INC., Los Angeles, CA (US)

(72) Inventors: Mark Hunter, Los Angeles, CA (US); Donald Armand Laprade, Los Angeles, CA (US)

(73) Assignee: Epic Inventing, Inc., Los Angeles, CA (US)

(*) Notice: Subject to any disclaimer, the term of this patent is extended or adjusted under 35 U.S.C. 154(b) by 361 days.

(21) Appl. No.: 17/291,060

(22) PCT Filed: Nov. 6, 2019

(86) PCT No.: PCT/IB2019/059547
§ 371 (c)(1),
(2) Date: May 4, 2021

(87) PCT Pub. No.: WO2020/095231
PCT Pub. Date: May 14, 2020

(65) Prior Publication Data
US 2021/0401596 A1 Dec. 30, 2021

Related U.S. Application Data

(60) Provisional application No. 62/756,205, filed on Nov. 6, 2018.

(51) Int. Cl.
*A61F 2/80* (2006.01)
*A61F 2/54* (2006.01)
(Continued)

(52) U.S. Cl.
CPC ............... *A61F 2/80* (2013.01); *A61F 2/583* (2013.01); *A61F 2/586* (2013.01); *A61F 2/70* (2013.01);
(Continued)

(58) Field of Classification Search
None
See application file for complete search history.

(56) References Cited

U.S. PATENT DOCUMENTS

| 5,108,455 A |   | 4/1992 | Telikicherla |
|---|---|---|---|
| 5,800,572 A | * | 9/1998 | Loveall ............... A61F 2/583 623/33 |

(Continued)

FOREIGN PATENT DOCUMENTS

| GB | 2103490 | 2/1983 |
|---|---|---|
| WO | 00/23016 | 4/2000 |

OTHER PUBLICATIONS

International Search Report and Written Opinion dated Feb. 19, 2020, from International Application No. PCT/IB2019/059547, 12 pages.

(Continued)

*Primary Examiner* — David H Willse
(74) *Attorney, Agent, or Firm* — Meunier Carlin & Curfman LLC

(57) ABSTRACT

The present invention provides a prosthetic socket (10) having a longitudinal axis X for attachment to a limb of a patient having first and second sides (A, B) which comprises a first portion (20) having a first edge (22), a second edge (24) a first end (26) and a second end (28) and second portion (30) having a first edge (32) a second edge (34) a first end (36) and a second edge (38). A hinge (40) is connecting the first edge (22) of the first portion (20) to the first edge (32) of the second portion (30) and a clasp (50) is provided between the second edge (24) of the first portion (20) and the second edge (34) of the second portion (30). Such an arrangement allows for a prosthetic socket (10) to be more easily attached and removed to a patients limb.

28 Claims, 5 Drawing Sheets

Socket open

(51) Int. Cl.
    *A61F 2/56*         (2006.01)
    *A61F 2/58*         (2006.01)
    *A61F 2/70*         (2006.01)
    *A61F 2/50*         (2006.01)
    *A61F 2/78*         (2006.01)

(52) U.S. Cl.
    CPC ............... *A61F 2002/5007* (2013.01); *A61F 2002/5026* (2013.01); *A61F 2002/5038* (2013.01); *A61F 2002/5039* (2013.01); *A61F 2002/587* (2013.01); *A61F 2002/701* (2013.01); *A61F 2002/785* (2013.01)

(56) References Cited

U.S. PATENT DOCUMENTS

| | | |
|---|---|---|
| 2007/0225824 A1 | 9/2007 | Einarsson |
| 2008/0275570 A1 | 11/2008 | Radzinsky |
| 2014/0039644 A1 | 2/2014 | Dillingham |
| 2017/0304086 A1* | 10/2017 | Kuiken ................. A61F 2/54 |
| 2018/0256365 A1 | 9/2018 | McCarron |

OTHER PUBLICATIONS

Combined Search and Examination Report under Sections 17 and 18(3) dated Apr. 23, 2019, from related GB Application No. 1819135.3, 5 pages.

\* cited by examiner

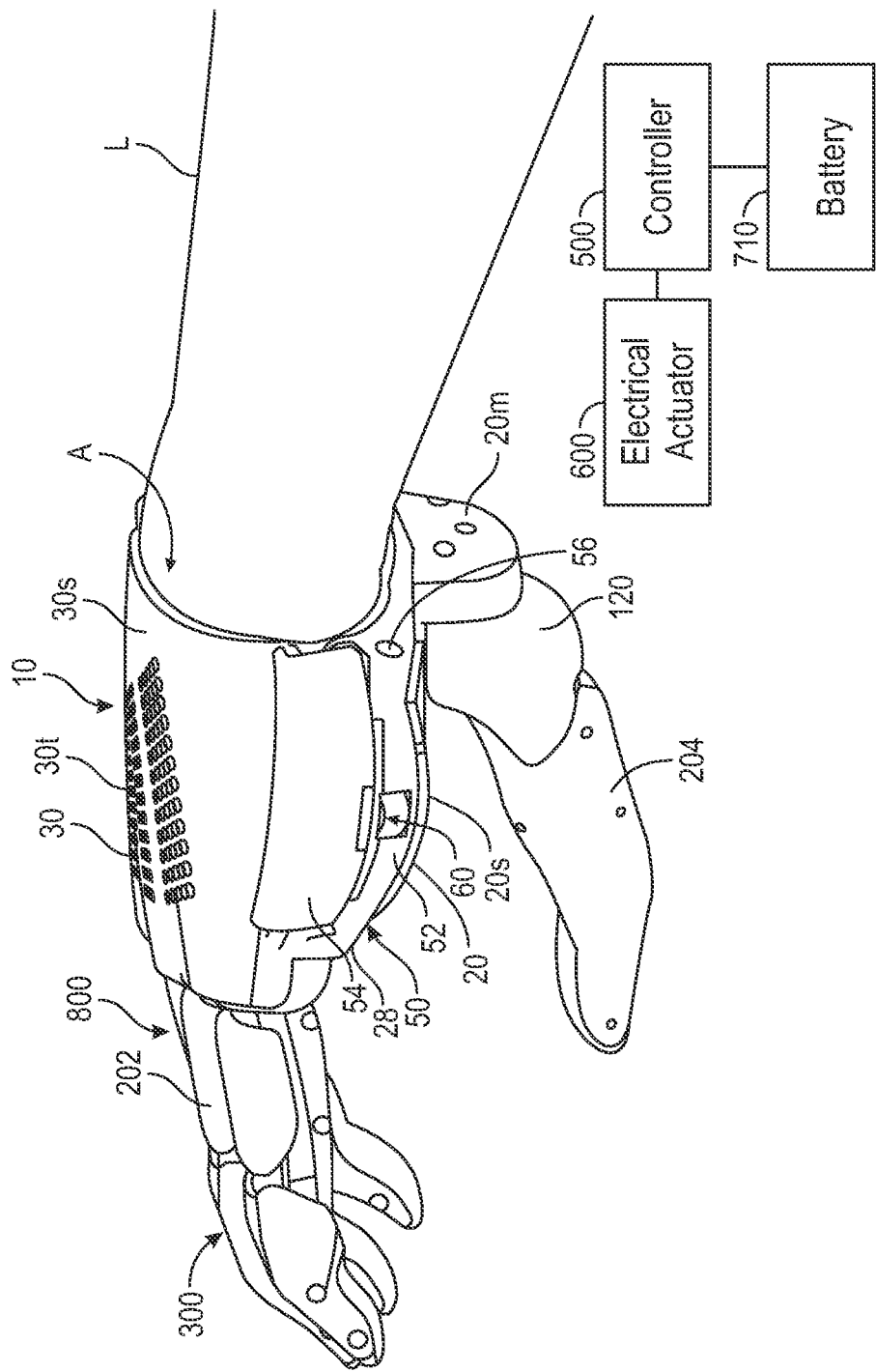
Fig 1 - Amputee arm with prosthetic fingers and socket with adjustable clasp

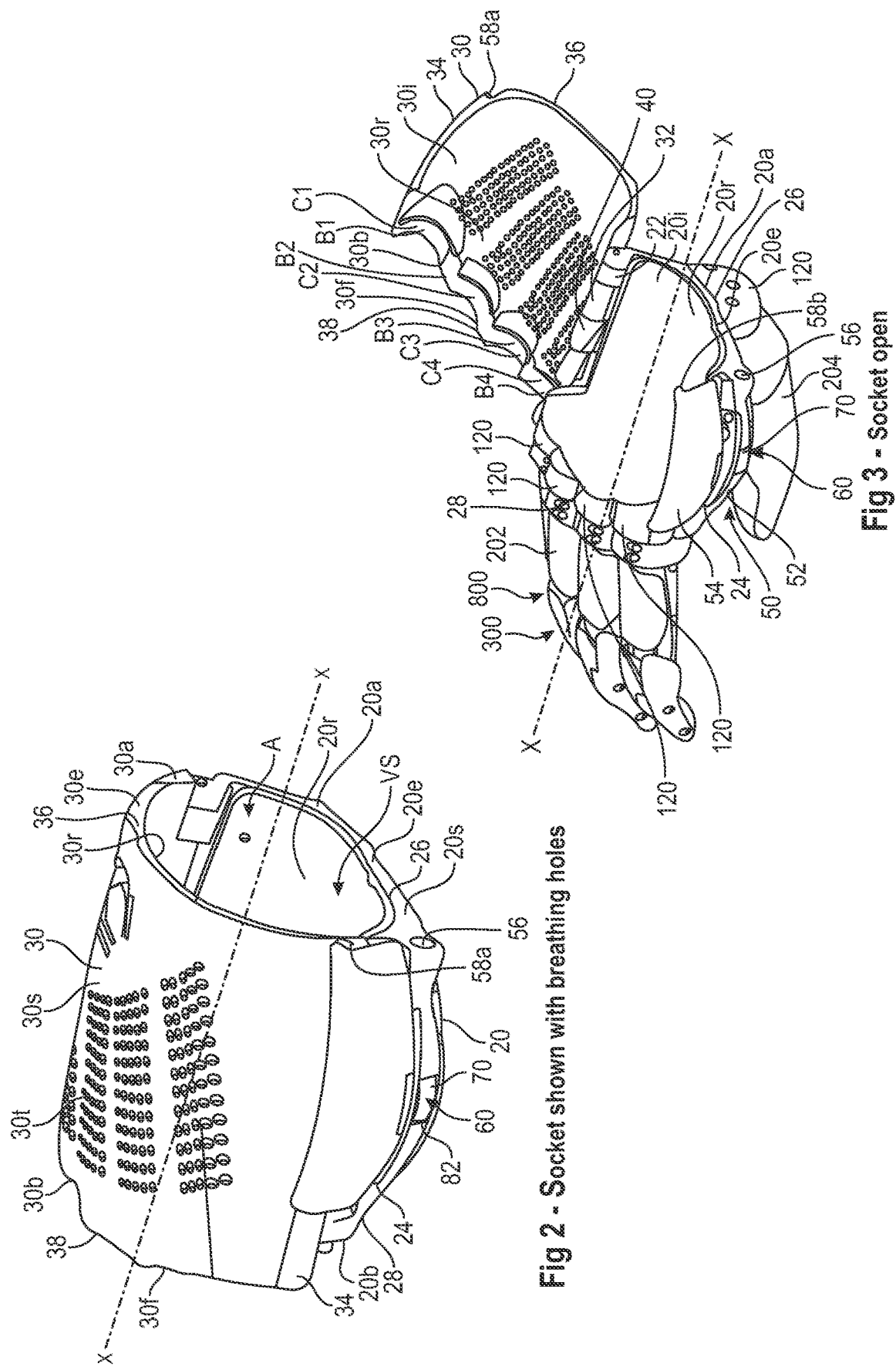
Fig 2 - Socket shown with breathing holes
Fig 3 - Socket open

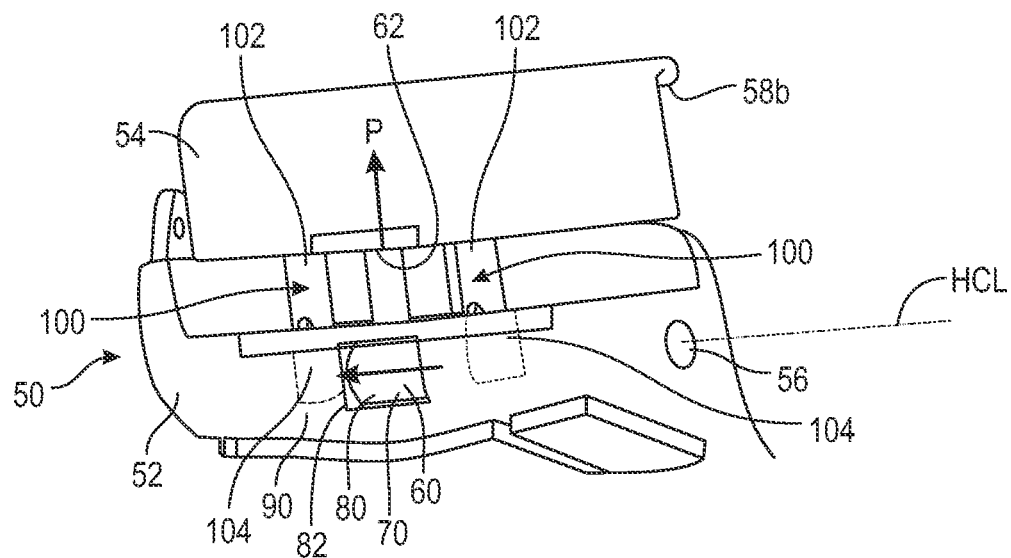
Fig 4 - Clasp extended position
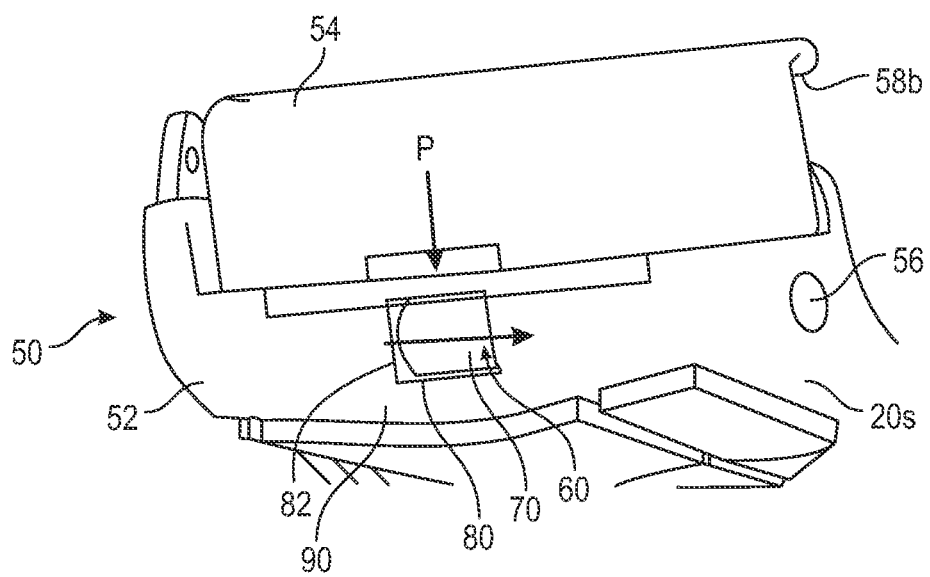
Fig 5 - Clasp retracted position

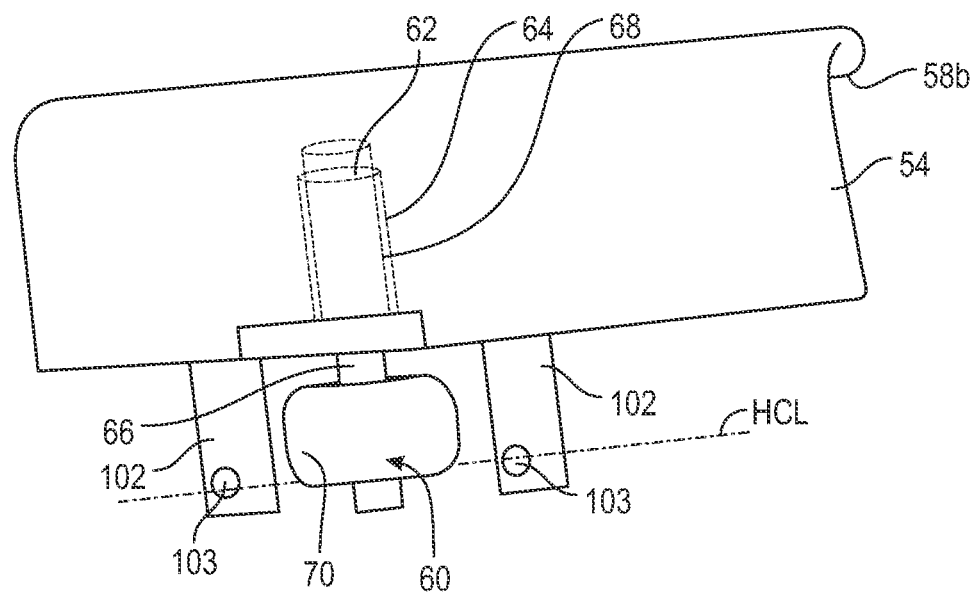
Fig 6 - Clasp showing internal detail
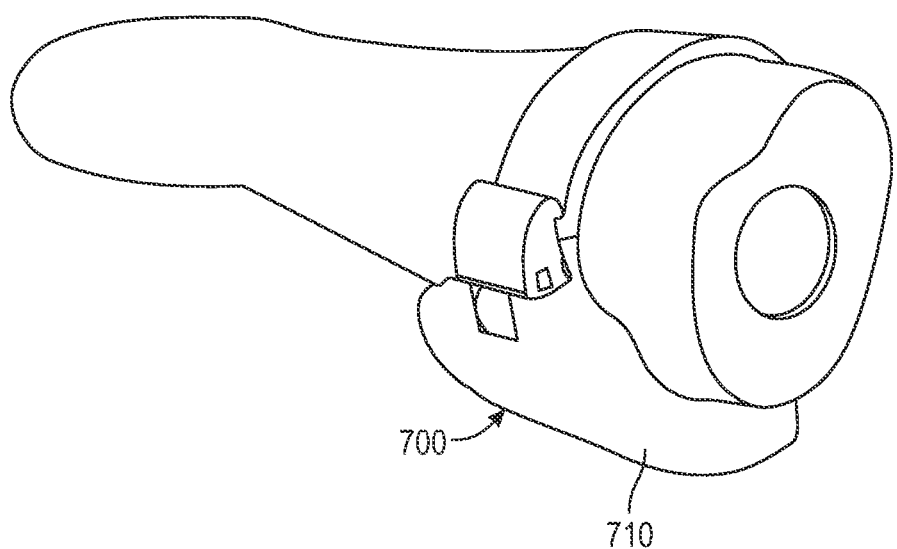
Fig 7 - Battery holder closed with amputees residual limb inside - holder is donned

PROSTHETIC SOCKET

CROSS-REFERENCE TO RELATED APPLICATIONS

This application is a United States National Phase Patent Application of International Patent Application Number PCT/IB2019/059547, filed on Nov. 6, 2019, which claims benefit of U.S. Provisional Application No. 62/756,205, filed on Nov. 6, 2018, both of which are incorporated by reference herein in their entireties.

The present invention relates to a prosthetic socket which can be used by amputees. The prosthetic socket can hold a prosthetic forearm, wrist, hand, or one or more digits and relates particularly but not exclusively to an arrangement having adjustability, so the socket may be made larger and smaller to accommodate residual limb volume change such as may be made for and used by human amputees and more particularly to those amputees that have lost a wrist, hand, or one or more digits on a hand. Such arrangements are generally referred to as "upper-limb" prosthetics. The present invention and elements thereof may also be used in or on a robotic device or exoskeleton device provided to support and assist a human being.

Prosthetic sockets are well known, such devices generally comprise parts which are made to be fitted to the user's residual limb. To date prosthetic sockets have tended to be one-piece arrangements which provide a sufficient fit to the user to keep the fingers, for example, attached to the user but prevent adjustment for comfort. In addition, applying and removing the socket is difficult as the socket is a push fit, so the user has to force their residual limb into the socket, which is often uncomfortable. In addition, since the socket is in one piece, cleaning is challenging, and hence the socket is often unhygienic. Examples in the prior art also include upper and lower portions which are hinged together and secured to each other by means of a clasp which is generally of a type as to prevent easy adjustment during use and can potentially cause unnecessary pain or discomfort to the user.

It is an object of the present invention to provide a prosthetic socket which improves over the known devices. In one arrangement the newly described device can be adjusted by a one-handed user thus maintaining a comfortable fit during the day and allowing for the easy applying and removing of the device and good hygiene. In the example of the present invention, a prosthetic socket may be provided with two portions, upper and lower, hinged to each other and fitted to the residual limb of the user. The lower portion is generally stiff and holds the fingers, whilst the upper portion is more flexible. On one side, the upper and lower portions are hinged to allow the user to easily don and doff the prosthetic. On the opposing side the upper and lower portions are connected with a catch, which can be open and closed with a wheel connected to a screw. A one handed user can easily don the prosthetic socket by placing their residual limb inside the open upper and lower portions, closing the portions together, then rolling the wheel which tightens the screw and catch, thus closing the prosthetic socket to a comfortable level of tightness. During the day the residual limb expands and contracts. By rolling the wheel in the desired direction the prosthetic socket can be expanded and contracted to facilitate a comfortable fit for the user. Such expansion and contraction is facilitated through micro-adjustment via the screw thread and such a degree of adjustment is not present in the prior art arrangements. The present invention, therefore, provides for even the most minor adjustment of the clamping effect throughout the day as and when desired by the user without the need to completely loosen the securing means.

Accordingly, the present invention provides a prosthetic socket having a longitudinal axis X for attachment to a limb of a patient, said socket having first and second sides (A, B) comprising; a first portion having a first edge, a second edge, a first end, and a second end; a second portion having a first edge, a second edge, a first end, and a second end and a hinge connecting the first edge of the first portion to the first edge of the second portion; and a clasp between the second edge of the first portion and the second edge of the second portion and wherein said clasp includes a screw thread adjuster for adjusting the position of the second portion relative to the first portion.

The hinge will allow the socket to be opened to allow easy insertion of the limb of the patient and closure around the limb whilst the clasp will allow for the securing together of the two sides of the socket once the limb is inserted. The screw thread adjuster on the clasp will allow for the micro adjustment of the clamping force on the limb so as to adjust for comfort and grip throughout the day. This second aspect is of particular importance as a user's limb will swell and change shape during the day and easy adjustment of the gripping force for comfort without having to completely undo the clamp will mean that the user will continue to have optimum support and grip without the discomfort normally associated with other forms of clasps.

Said clasp may include an adjuster for adjusting the position of the second portion relative to the first portion. In one arrangement the clasp includes a fixed portion and a movable portion movable between a first (retracted) position and a second (extended) position and wherein said fixed portion is mounted on said first portion and wherein said movable portion is movable in a direction P generally perpendicular to axis X towards and away from said second portion.

In an easily applied arrangement, the clasp includes a hinge connecting said fixed portion to said first portion. This arrangement allows the two portions to be opened-up relative to each other such as to allow more convenient access to the interior of the socket and easy insertion of the limb of a user.

The second portion of the socket may include a first interlocking member and the movable portion of said clasp may include a second interlocking member. In use these interlocking members may be caused to engage with each other such as to maintain the device closed around a patient's limb.

The adjuster may comprise a first aperture on said movable portion and may be provided with a screw thread therein and the adjuster may further include a threaded bar having a thread and extending from said fixed portion and into said aperture. The threaded bar may include a roller portion attached to and rotatable with said threaded bar whilst said fixed portion may include a second aperture through which said threaded bar extends and said fixed portion may include an outer surface and a recess within the outer surface containing said roller portion. Said roller portion may extend outward of said outer surface or may remain recessed below the outer surface.

There may be provided a guide for guiding said movable portion between said first (retracted) position and said second (extended) position. When provided, the guide may include one or more projections and one or more apertures into which said projections extend. The one or more projections may extend from said movable portion and said one or more apertures may extend into said fixed portion.

Alternatively, said one or more projections may extend from said fixed portion and said one or more apertures may extend into said movable portion.

The first interlocking member and said second interlocking member may comprise axially extending ridges.

The device may include one or more mounting points for receiving one or more prosthetic digits.

In a particular arrangement said first portion includes a first proximal end and said second portion includes a first proximal end and a second distal end, wherein said proximal first ends and said first and second portions include concave interior surfaces which confront each other to define an interior void space, wherein said respective ends comprise curved edges, which between them define a first aperture through which the limb of a user may be inserted.

In a particular arrangement said first portion includes a second distal end and said second portion includes a first proximal end and a second distal end and said first and second portions include concave interior surfaces which confront each other to define an interior void space and said respective distal ends comprise multiple curved edges which between them define multiple second apertures for receiving respective artificial digits. Such digits may replicate fingers.

In one arrangement the first portion includes a first proximal end and an outer surface and said prosthetic device further includes a mounting point at the first proximal end on the outer surface for receiving an artificial digit in the form of, for example, an artificial thumb.

The first and second portions may include concave interior surfaces which confront each other to define an interior void space. One or more of said concave interior surfaces may include a resiliently deformable surface. Such a surface may allow for the accommodation of variations in limb size and/or provide a better grip on the limb itself.

In one arrangement the first and second portions include inner surfaces and outer surfaces and further include a plurality of breather apertures extending through one or other of said first or second portions from respective inner surfaces to respective outer surfaces. Such apertures will assist with cooling and also potentially moisture transfer and may be positioned as and where appropriate across the surfaces.

The resiliently deformable surface may comprise an open cellular material such as to allow for the passage of heat and/or moisture therethrough.

In a particular arrangement one or other or both of said first or second portions comprises a resiliently deformable material.

The device may include a plurality of prosthetic digits attached thereto. When such digits are provided, they may be provided in the form of controllable mechanical digits or simply prosthetic replacements which are not controllable, but which are visually impactful.

A controller may be provided and linked to one or more of said controllable mechanical digits for controlling said one or more mechanical digits.

The controllable mechanical digits may each include an electric actuator for causing movement thereof and said controller may be operably connected to one or more of said electric actuators for initiating control thereof.

The device may further include a separate holder for holding one or more batteries and wherein said device includes one or more mechanical digits each having an electric actuator and wherein said one or more batteries are connected for supplying electricity to one or more of said one or more electrical actuators. Said holder may further include the controller linked to one or more of said controllable mechanical digits for controlling said one or more mechanical digits.

According to another aspect of the present invention there is provided a prosthetic socket having a longitudinal axis X for attachment to a limb of a patient having first and second sides (A, B), comprising: a first portion having a first edge, a second edge, a first end, and a second end, and may also include a second portion having a first edge, a second edge, a first end, and a second end. A hinge may connect the first edge of the first portion to the first edge of the second portion. A clasp may be provided between the second edge of the first portion and the second edge of the second portion and said clasp may include a screw thread adjuster for adjusting the position of the second portion relative to the first portion. Said screw thread adjuster may comprise a first aperture on said movable portion having a screw thread therein and a threaded bar having a thread and extending from said fixed portion and into said aperture.

In either of the above arrangements, said clasp may be connected to and extend from the second edge of the first portion and connect to and extend from the second edge of the second portion.

In either of the above arrangements the first portion may comprise a profiled portion having a profile matching a first surface of a human hand and said second portion may comprise a profile matching a second surface of a human hand.

According to another aspect of the present invention there is provided a prosthetic socket having a longitudinal axis X for attachment to a limb of a patient having first and second sides (A, B), comprising: a first portion having a first edge, a second edge, a first end, and a second end; a second portion having a first edge, a second edge, a first end, and a second end; a hinge connecting the first edge of the first portion to the first edge of the second portion; a clasp between the second edge of the first portion and the second edge of the second portion and wherein said clasp includes a screw thread adjuster for adjusting the position of the second portion relative to the first portion and wherein said screw thread adjuster comprises a first aperture on said movable portion having a screw thread therein and a threaded bar having a thread and extending from said fixed portion and into said aperture; and wherein said first portion comprises a profiled portion having a profile matching a first surface of a human hand and said second portion comprises a profile matching a second surface of a human hand.

The present invention and elements thereof may be applied to a human or animal body or to a robotic device or exoskeleton device provided to support and assist a human being.

Aspects of the present invention will now be more particularly described by way of example only with reference the accompanying drawings, in which:

FIG. 1 is a general view of a prosthetic socket incorporating elements of the present invention and is shown as attached to a human limb;

FIG. 2 is a more detailed view of the socket of FIG. 1 in a closed arrangement;

FIG. 3 is a detailed view of the socket of FIG. 1 in an open configuration and showing a plurality of prosthetic digits attached thereto;

FIGS. 4 and 5 illustrate in more detail a clasp arrangement which may be applied to the prosthetic device shown in FIG. 1 and show the clasp in an extended and retracted configuration;

FIG. 6 is a partial cross-sectional view of a portion of the clasp shown in FIGS. 4 and 5;

FIG. 7 is a perspective view of a battery arrangement which may be used to power prosthetic digits which may be attached to the prosthetic socket of the above figures.

Figure 8:
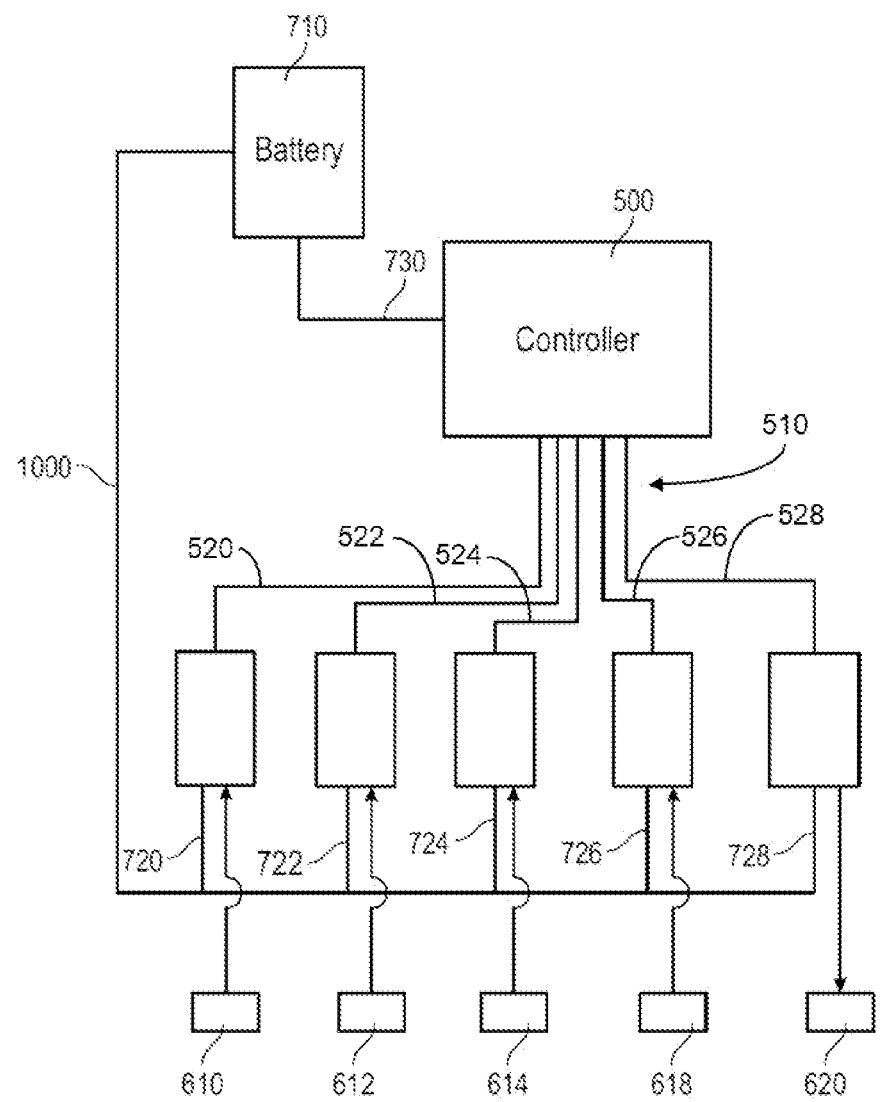
FIG. 8 is a schematic representation of the connections between the various devices mentioned within this application.

Referring now to the drawings in general but particularly to FIGS. 1 to 3, a prosthetic socket has a longitudinal axis X and is used to enclose a first and second side (A,B) of a limb of a patient. The socket 10 includes a first and a second portion 20, 30. The first portion 20 having a first edge 22 and a second edge 24, a first end 26 and a second end 28 which, between them, act to define the boundary of the first portion 20. The second portion 30 also includes a first edge 32, a second edge 34, a first end 36, and a second end 38, which between them act to define the boundary of the second portion 30. The first and second portions 20, 30 effectively act to provide lower and upper covers respectively which, in operation, encase the limb of the patient, as shown in FIG. 1. Whilst it will be appreciated that the two portions 20, may be connected in any number of ways, it has been found that the provision of a hinge connecting the first edge 22 of the first portion 20 to the first edge 32 of the second portion is of significant benefit as such an arrangement allows the limb L of the patient to be easily inserted and removed from within the socket 10. A clasp 50 or any other form of securing member is preferably provided to hold the two portions 20, 30 together as and when they are closed around, for example, the limb of a patient. Such a clasp may be provided between the second edge 24 of the first portion 20 and the second edge 34 of the second portion 30 as shown in FIG. 1 but may also be provided by means of a strap or a Velcro fastener (hook and eye connector) or other such fastening extending between the two portions 20, 30. In a preferred arrangement the clasp comprises an adjustable clasp 50 such as to allow for the accommodation of different sized limbs L or to allow for the adjustment of any clamping force that may be placed around the limb L. Such adjustment may be required throughout the day as the patient's limb L expands or contracts due to the ambient temperature or for other reasons such as the comfort of the patient or to improve blood-flow. A velcro strap is very adjustable but may not provide the degree of assurance of grip between the socket 10 and the patient's limb L as may be required in intense usage. For this and other reasons it may be desirable to provide the clasp 50 in the form of a more rigid but adjustable connection between the two portions 20, 30. Such a device is shown briefly in FIGS. 1 to 3 and in more detail in FIGS. 4 to 6 and includes a fixed portion 52 and a movable portion 54 which is movable between a first retracted position R and a second extended position E. Preferably, the fixed portion 52 is mounted on said first portion 20 and the movable portion 54 is mounted for movement relative thereto, but the arrangement may be the other way around. The clasp as shown in FIGS. 2 and 3 includes a first interlocking member 58a on the second portion 30 of the socket 10 and the movable portion 54 of the clasp 50 includes a second interlocking member 58b which, in operation, interacts with the first interlocking member 58a when securing the clasp 50 to the second portion 30 of the socket 10. Such an interlocking arrangement may simply comprise returned edge portions which are complementarily shaped such as to interlock with each other when placed in contact with each other. An adjuster shown generally at 60 is provided for adjusting the position of the second portion 30 of the socket 10 relative to the first portion 20 and such an adjuster may be incorporated into the clasp 50. In effect, the adjuster 60, when incorporated into the clasp 50, provides a mechanism for moving the movable portion 54 of the clasp 50 and hence the second portion 30 of the socket 10 nearer or further away from the first portion 20 of the socket. Such movement will, in effect, adjust the volume of any void space VS within the interior of the socket 10 and, hence, adjust the clamping force on any limb L placed therein. The adjuster 60 is best seen in FIGS. 4 to 6 and includes a first aperture 62 on the movable portion 54 having a screw thread 64 therein and a threaded bar 66 having an outer thread 68 provided thereon and extending from the fixed portion 52 of the clasp 50 and into the aperture 62 such as to allow threads 64 and 68 to inter-engage with each other. A roller portion 70 may be attached to said threaded bar 66 and said fixed portion 52 may include a second aperture 80 through which said threaded bar 66 extends and the fixed portion 52 may include an outer surface 90 and a recess 82 within the outer surface 90 containing said roller portion 70. The roller portion 70 preferably extends outward of said outer surface 90 such as to allow easy access thereto, but it may be recessed below the surface should that be desired for the purposes of preventing inadvertent actuation thereof.

Also shown in FIG. 4 is a guide shown generally at 100 for guiding the movable portion 54 between said first, retracted, and said second, extended, positions. Whilst it will be appreciated that the guide 100 may take any one of a number of forms, it has been found useful to include one or more projections 102 and one or more apertures 104 into which the projections 102 extend as one beneficial way of providing smooth movement. In the arrangement of FIGS. 4 and 6 the projections 102 are provided on movable portion 54 whilst the corresponding apertures 104 are provided within and extend into said fixed portion 52, although the arrangement may be the opposite way around if so desired.

The first and second interlocking members 58a, 58b mentioned above with reference to FIG. 4 may comprise axially extending ridge portions extending along an axis X1. Such axis X1 may be parallel to the main axis X of the device itself 10 or may be arranged orthogonal thereto if so desired. Axis X1 may be curved so as to conform to any external profile of the device 10 but is preferably straight as such would allow for a more positive engagement between the two interlocking members 58a, 58b.

Referring now once again to FIGS. 1 and 3, the device 10 may further include one or more mounting points 120 for receiving a prosthetic digit in the form of, for example fingers 202 and thumb 204 referenced generically as 300. Such prosthetic digits may be mounted to the socket in any one of a number of ways but the following approach has been found to be most beneficial as the digits are easily incorporated into the socket 10 as and where desired and if the human patient has one or more digits remaining the natural digits may be accommodated within the socket 10 such as to allow the user to continue using their existing digits alongside any supplemental prosthetic digits. It will also be appreciated that the prosthetic digits may be actuated or non-actuated digits but that actuated digits are most preferred.

In the arrangement according to aspects of the present invention said proximal first ends 26, 36 and said first and second portions 20, 30 may include concave interior surfaces 20i and which confront each other to define an interior void space VS and the respective ends 26, 36 may comprise curved edges which, between them, define a first aperture (A) through which the limb (L) of a user may be inserted.

The respective distal ends (28, 38) may comprise multiple curved edges (C1, C2, C3, C4) which between them define multiple second apertures (B1, B2, B3, B4) for receiving respective artificial digits (300) or for allowing any remaining natural digits to be incorporated into the prosthetic socket and extend therefrom. An outer surface (20s) of the first portion 20 may further include a mounting point (20m) at the first proximal end (26) thereof for receiving an artificial digit (300) such as, for example, an artificial thumb 204. Alternatively, this may be omitted if the patient has a retained natural thumb and a space provided so as to allow the natural thumb to project from the socket. In order to accommodate the shape of the limb to which the socket 10 is to be applied, the first and second portions (20, 30) may include concave interior surfaces (20i, 30i) which confront each other to define an interior void space (VS) into which the patient's limb may be inserted and between which the limb may be captured. The one or more of said interior surfaces (20i, 30i) may further include a resiliently deformable surface (20r, 30r) as such will allow the two portions 20, 30 to be comfortably placed around a patient's limb L without applying undue pressure at any one point and will also allow a degree of clamping force and resistance to movement to be incorporated into the design. If desired, one may provide the inner surfaces (20i, 30i) and outer surfaces (20s, 30s) with a plurality of breather apertures (20t, 30t) extending through one or other or both of said first or second portions (20, 30) from respective inner surfaces (20i or 30i) to respective outer surfaces (20s, 30s). Such apertures would allow the patient's limb to be cooled and, hence, contribute to the general comfort of the patient. When provided, the resiliently deformable surface (20r, 30r) may comprise an open cellular material or porous material or a material with a plurality of holes extending therethrough, as such may allow for the passage of heat therethrough and further enhance the general comfort of the patient. Whilst the first and second portions 20, 30 may be of a relatively rigid construction such as to ensure rigidity of clamping around the patient's limb L, it will also be appreciated that a degree of flexibility may also be desirable and, hence, the first and second portions 20, 30 may, themselves, be made of resilient material such as to provide a degree of flexure and, hence, better fit around the patient's limb.

The arrangement of the drawings shows the socket 10 provided with a full complement of prosthetic digits 300 and one or more of these may comprise controllable mechanical digits referenced generally at 800. Such controllable digits 800 are well known and may comprise any one of a number of forms, some of which are provided by the current applicant and described in other publications or patent applications of the present applicant. When provided, such controllable digits 800 would be connected to a controller 500 by means of control lines shown generally at 510 and such a controller would be used to control the controllable digits 800 in the manner well known in the art and, therefore, not described herein. The present invention does, however, include one or more controllable digits 800 and each includes an electric actuator shown collectively at 600 and individually at 610, 612, 614, 616, 618, 620. Each digit 800 is individually or collectively controlled by the controller 500 in accordance with well-known control methodologies.

It will be appreciated that the controller 500 may be mounted on the socket 10 itself but it may be more convenient to mount the controller 500 remotely and, if provided remotely, the controller 500 may be provided within a separate holder (700) which may also be used for holding one or more batteries (710). Such batteries may provide power to the controller 500 as well as one or more of the electric actuators 600 and, as such, said one or more batteries (710) are connected for supplying electricity to one or more of said one or more electrical actuators (600) by means of power lines 1000 shown schematically only in FIG. 8.

Referring now more particularly to FIG. 7, the present invention also provides a separate holder 700 and such a container 700 may be secured to the patient's arm or another limb L remote from the prosthetic socket. Such a location may include under the patient's clothing such as to hide the container and any batteries or controller that may be provided therein. Such an arrangement would help reduce the physical size of the prosthetic socket 10 and help to create a more aesthetically pleasing and more anatomically correct product.

FIG. 8 shows the general arrangement of connections between various components of the present invention and from which it will be appreciated that if controllable digits 800 are to be used, each will require an electrical supply from the battery 710 or other means of power as well as a control connection to the controller 500. The power is provided by means of power lines 720, 722, 724, 726, 728 whilst the control connections are provided by means of control lines 520, 522, 524, 526, 528. The controller 500 may also be supplied with power from the battery 710 and power line 730 is provided for this purpose.

The above describes the socket 10 and various components associated therewith and shows how such a socket 10 could be used to mount prosthetic digits 300. The shape of the limb L to which such a socket 10 may be attached will, however, vary and, hence, the void space VS may usefully be tailored to suit individual needs. For example, one may machine the interior surfaces 20i, 30i to match the profile of the limb. Alternatively, one may mount the two portions 20, 30 around the limb or a facsimile thereof. Alternatively, and possibly more usefully, one may manufacture each of portions 20 and 30 to match the shape and profile of the patient's limb before assembly, thus making a truly bespoke product. Advances in rapid prototyping machines and CNC machining make such options readily available to a manufacturer of such devices and the scanning of a patient's limb before the manufacturing commences is now possible by many means. The concept described herein would allow for the scanning of a patient's limb to be done in one location and the manufacture to be done in another without the patient actually having to move away from their home location or hospital.

Operation of the above-mentioned device will now be described with reference to the drawings in general but with particular reference to FIGS. 1 to 7. The two portions 20 and 30 are first opened by moving them relative to hinge 40 such as to expose the interior surfaces 20i, 30i before the limb L of a patient is inserted therebetween. Once the limb L is appropriately positioned, the two portions 20, 30 may be closed around the limb L by simply moving them towards each other and pivoting them around hinge 40. As the two portions come closer towards each other the user will adjust the position of the limb L such that it sits comfortably up against the interior surfaces 20i, 30i. The clasp 50 may be used to secure the two portions together by simply causing the first and second interlocking members 58a, 58b to engage with each other and then interlock. Interlocking is achieved by adjusting the position of movable portion 54 relative to the second portion 30 and this may be done by causing actuation of the adjuster 60. The adjuster 60 includes a roller 70 connected to a threaded bar 66 which, in turn, is screw threadedly connected to the screw thread 64 within aperture 62 of the movable portion 54. Turning roller 70 will cause the screw threads to tighten relative to each other and cause the movable portion 54 to move closer to the fixed portion 52 on portion 20. This action acts to simply close the two portions 20, 30 relative to each other and capture any limb therebetween. Once the patient's limb is secure within the socket 10 the battery pack and controller may be connected to the digits 300 such as to allow for the operation thereof in accordance with well-known processes. The battery pack may incorporate the same clamping mechanism as the prosthetic socket, so it too can be adjusted for comfort during the day.

The above device may be adjusted in use by simply increasing or reducing the clamping force created by the clasp 50. Such adjustment may be necessary as the patient's limb warms and expands or cools and contracts but may also be required if the patient simply wishes to have a more secure grip on the limb.

It will be appreciated that elements of the present invention may be used in the singular or in combination with other elements described herein. It will also be appreciated that the present invention and elements thereof may be used in or on a robotic device or exoskeleton device provided to support and assist a human being.

The invention claimed is:

1. A prosthetic socket having a longitudinal axis X for attachment to a limb of a patient having first and second sides (A, B) comprises:
    a) a first portion having a first edge, a second edge, a first end, and a second end;
    b) a second portion having a first edge, a second edge, a first end, and a second end;
    c) a hinge connecting the first edge of the first portion to the first edge of the second portion; and
    d) a clasp between the second edge of the first portion and the second edge of the second portion and wherein said clasp includes a screw thread adjuster for adjusting the position of the second portion relative to the first portion.

2. A prosthetic socket as claimed in claim 1, wherein said clasp includes a fixed portion and a movable portion movable between a first (retracted) position and a second (extended) position and wherein said fixed portion is mounted on said first portion and wherein said movable portion is movable in a direction P generally perpendicular to axis X towards and away from said second portion.

3. A prosthetic socket as claimed in claim 2 and wherein said second portion of the socket includes a first interlocking member and the movable portion of said clasp includes a second interlocking member.

4. A prosthetic device as claimed in claim 3 and wherein said first interlocking member and said second interlocking member comprise axially extending ridges.

5. A prosthetic device as claimed in claim 2 and wherein said adjuster comprises a first aperture on said movable portion having a screw thread therein and a threaded bar having a thread and extending from said fixed portion and into said aperture.

6. A prosthetic device as claimed in claim 5 and wherein said threaded bar includes a roller portion attached to and rotatable with said threaded bar, said fixed portion includes a second aperture through which said threaded bar extends and said fixed portion includes an outer surface a recess within the outer surface containing said roller portion and wherein said roller portion extends outward of said outer surface.

7. A prosthetic device as claimed in claim 2 and including a guide for guiding said movable portion between said first (retracted) position and said second (extended) position.

8. A prosthetic device as claimed in claim 7, wherein said guide includes one or more projections and one or more apertures into which said projections extend.

9. A prosthetic device as claimed in claim 8, wherein said one or more projections extend from said movable portion and said one or more apertures extend into said fixed portion.

10. A prosthetic device as claimed in claim 9, wherein said one or more projections extend from said fixed portion and said one or more apertures extend into said movable portion.

11. A prosthetic device as claimed in claim 1 and including one or more mounting points for receiving a prosthetic digit.

12. A prosthetic device as claimed in claim 1 and wherein said first portion includes a first proximal end and said second portion includes a first proximal end and a second distal end and wherein said proximal first ends and said first and second portions include concave interior surfaces which confront each other to define an interior void space (VS) and wherein said respective ends comprise curved edges which between them define a first aperture (A) through which the limb (L) of a user may be inserted.

13. A prosthetic device as claimed in claim 1 and wherein said first portion includes a second distal end and said second portion includes a first proximal end and a second distal end and said first and second portions include concave interior surfaces which confront each other to define an interior void space (VS) and wherein said respective distal ends comprise multiple curved edges (C1, C2, C3, C4) which between them define multiple second apertures (B1, B2,B3,B4) for receiving respective artificial digits.

14. A prosthetic device as claimed in claim 1 and in which said first portion includes a first proximal end and an outer surface and wherein said prosthetic device further includes a mounting point at the first proximal end on the outer surface for receiving an artificial digit.

15. A prosthetic device as claimed in claim 1 and wherein said first and second portions include a concave interior surfaces which confront each other to define an interior void space (VS) and wherein one or more of said convex concave interior surfaces include a resiliently deformable surface.

16. A prosthetic device as claimed in claim 1 and wherein said first and second portions include inner surfaces and outer surfaces and further include a plurality of breather apertures extending through one or other of said first or second portions from respective inner surfaces to respective outer surfaces.

17. A prosthetic device as claimed in claim 15 and wherein said resiliently deformable surface comprises an open cellular material (such as to allow for the passage of heat therethrough).

18. A prosthetic device as claimed in claim 1 and wherein one or other of said first or second portions comprise resiliently deformable material.

19. A prosthetic device as claimed in claim 1 and including a plurality of prosthetic digits attached thereto.

20. A prosthetic device as claimed in claim 19 and wherein said prosthetic digits comprise controllable mechanical digits.

21. A prosthetic device as claimed in claim 20 and including a controller linked to one or more of said controllable mechanical digits for controlling said one or more mechanical digits.

22. A prosthetic device as claimed in claim 20 and wherein said controllable mechanical digits each include an electric actuator for causing movement thereof and wherein said controller is operably connected to one or more of said electric actuators for initiating control thereof.

23. A prosthetic device as claimed in claim 1 and including a separate holder for holding one or more batteries and wherein said device includes one or more mechanical digits each having an electric actuator and wherein said one or more batteries are connected for supplying electricity to one or more of said one or more electrical actuators.

24. A prosthetic device as claimed in claim 23 and wherein said holder further includes including a controller linked to one or more of said controllable mechanical digits for controlling said one or more mechanical digits.

25. A prosthetic socket as claimed in claim 1 and wherein said clasp is connected to and extends from the second edge of the first portion and connected to and extends from the second edge of the second portion.

26. A prosthetic socket as claimed claim 1 and wherein said first portion comprises a profiled portion having a profile matching a first surface of a human hand and said second portion comprises a profile matching a second surface of a human hand.

27. A prosthetic socket having a longitudinal axis X for attachment to a limb of a patient having first and second sides (A, B) comprises:
   e) a first portion having a first edge, a second edge, a first end, and a second end;
   f) a second portion having a first edge, a second edge, a first end, and a second end;
   g) a hinge connecting the first edge of the first portion to the first edge of the second portion; and
   h) a clasp between the second edge of the first portion and the second edge of the second portion and wherein said clasp includes a screw thread adjuster for adjusting the position of the second portion relative to the first portion and wherein said screw thread adjuster comprises a first aperture on a clasp movable portion having a screw thread therein and a threaded bar having a thread and extending from a clasp fixed portion and into said aperture.

28. A prosthetic socket having a longitudinal axis X for attachment to a limb of a patient having first and second sides (A, B) comprises:
   i) a first portion having a first edge, a second edge, a first end, and a second end;
   j) a second portion having a first edge, a second edge, a first end, and a second end;
   k) a hinge connecting the first edge of the first portion to the first edge of the second portion; and
   l) A clasp between the second edge of the first portion and the second edge of the second portion and wherein said clasp includes a screw thread adjuster for adjusting the position of the second portion relative to the first portion and wherein said screw thread adjuster comprises a first aperture on a clasp movable portion having a screw thread therein and a threaded bar having a thread and extending from a clasp fixed portion and into said aperture; and wherein
   m) said first portion comprises a profiled portion having a profile matching a first surface of a human hand and said second portion comprises a profile matching a second surface of a human hand.

* * * * *